(12) United States Patent
Dykers

(10) Patent No.: US 8,347,695 B1
(45) Date of Patent: Jan. 8, 2013

(54) MEAT TENDERNESS TESTER

(76) Inventor: John R. Dykers, Siler City, NC (US)

( * ) Notice: Subject to any disclaimer, the term of this patent is extended or adjusted under 35 U.S.C. 154(b) by 0 days.

(21) Appl. No.: 13/309,368

(22) Filed: Dec. 1, 2011

(51) Int. Cl.
  *G01N 3/48* (2006.01)
  *G01N 3/32* (2006.01)
  *G01N 33/02* (2006.01)
(52) U.S. Cl. .................................. 73/81; 73/83; 426/231
(58) Field of Classification Search ............... 73/81, 83; 426/231
  See application file for complete search history.

(56) References Cited

U.S. PATENT DOCUMENTS

| 2,446,956 A | | 8/1948 | Ross |
| 3,214,967 A | | 11/1965 | Bouschart et al. |
| 3,308,654 A | | 3/1967 | Badgley |
| 3,554,018 A | | 1/1971 | Anderson et al. |
| 3,688,566 A | * | 9/1972 | Hansen .............................. 73/78 |
| 3,956,924 A | | 5/1976 | Hansen et al. |
| 4,052,890 A | * | 10/1977 | Kammlah et al. ................. 73/81 |
| 4,939,927 A | * | 7/1990 | Johnston ............................ 73/81 |
| 2010/0221395 A1 | | 9/2010 | Meullenet |

FOREIGN PATENT DOCUMENTS

WO   WO 91/19976 A1   12/1991

* cited by examiner

*Primary Examiner* — Lisa Caputo
*Assistant Examiner* — Jamel Williams
(74) *Attorney, Agent, or Firm* — Richard C. Litman

(57) ABSTRACT

The meat tenderness tester is a hand held tool that includes a rotatable elongate shaft, which can be stuck into meat at a precise depth and rotated by a motor disposed in the tool. The shaft has various configurations that allow it to be inserted into the meat and withdrawn without destroying the meat being tested. Fin-like members disposed on the shaft create a measurable resistance to rotation that is measured by a torque sensing part of the motor. A digital display on the housing body reads out this mechanical resistance (torque) in a calibrated measurement of the shear forces encountered by the rotating shaft; the measurement indicating a degree of tenderness of the meat cut being tested. The shaft has a tapered, pointed end that allows it to be inserted and withdrawn without damaging the meat product under test.

7 Claims, 4 Drawing Sheets

MEAT TENDERNESS TESTER

BACKGROUND OF THE INVENTION

1. Field of the Invention

The present invention relates to meat testers, and particularly to a rotating probe having torque measurements, which aid in classifying meat in respect of tenderness.

2. Description of the Related Art

Traditionally, meat, including beef, lamp and port, has generally been classified by means of inspection carried out preferably by a trained inspector. However, it is a disadvantage of this method that the classification is generally unreliable due to varying standards between inspectors, and that inspection is generally just a visual inspection.

Various devices have also been proposed to aid in detecting the tenderness of meat. These meat tenderness testers try to simulate meat cutting with a knife, then utilize the standard for tenderness testing which is the Warner-Bratzler shear test as known by skilled artisans. A problem with this test is that it is not suitable for quick testing on a beef or pork production line.

Thus, a meat tenderness tester solving the aforementioned problems is desired.

SUMMARY OF THE INVENTION

The meat tenderness tester is a hand held tool that includes a rotatable elongate shaft, which can be stuck into meat at a precise depth and rotated by a motor disposed in the tool. The shaft has various configurations that allow it to be inserted into the meat and withdrawn without destroying the meat being tested. Fin-like members disposed on the shaft create a measurable resistance to rotation that is measured by sensors disposed inside housing body of the tool.

A digital display on the housing body reads out this mechanical resistance (torque) in a calibrated measurement of the shear forces encountered by the rotating shaft; the measurement indicating a degree of tenderness of the meat cut being tested. The shaft has a tapered, pointed end that allows it to be withdrawn without damaging the meat product under test.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
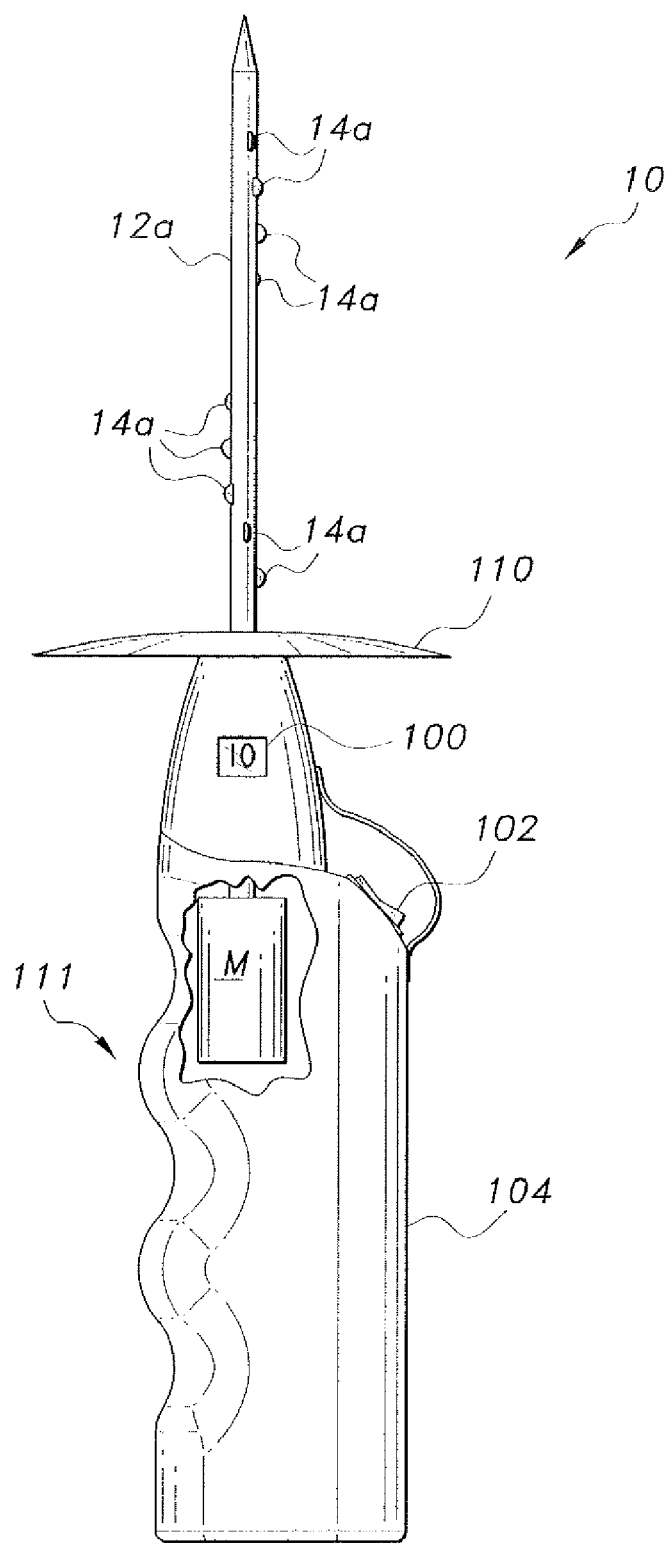
FIG. 1 is a plan view of the meat tenderness tester according to the present invention.
Figure 2:
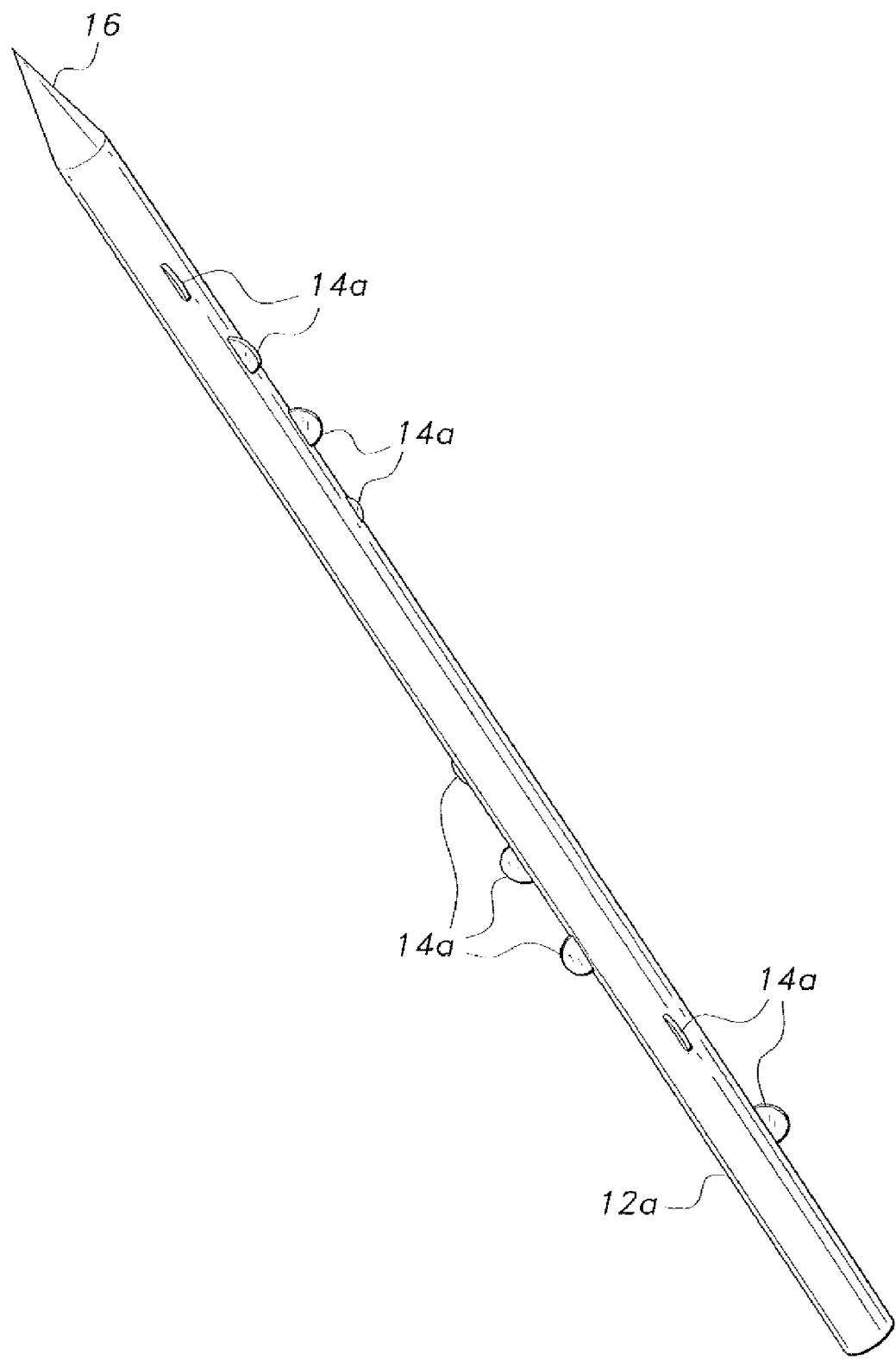
FIG. 2 is a perspective view of the shaft and helically arranged fins according to the present invention.
Figure 3:
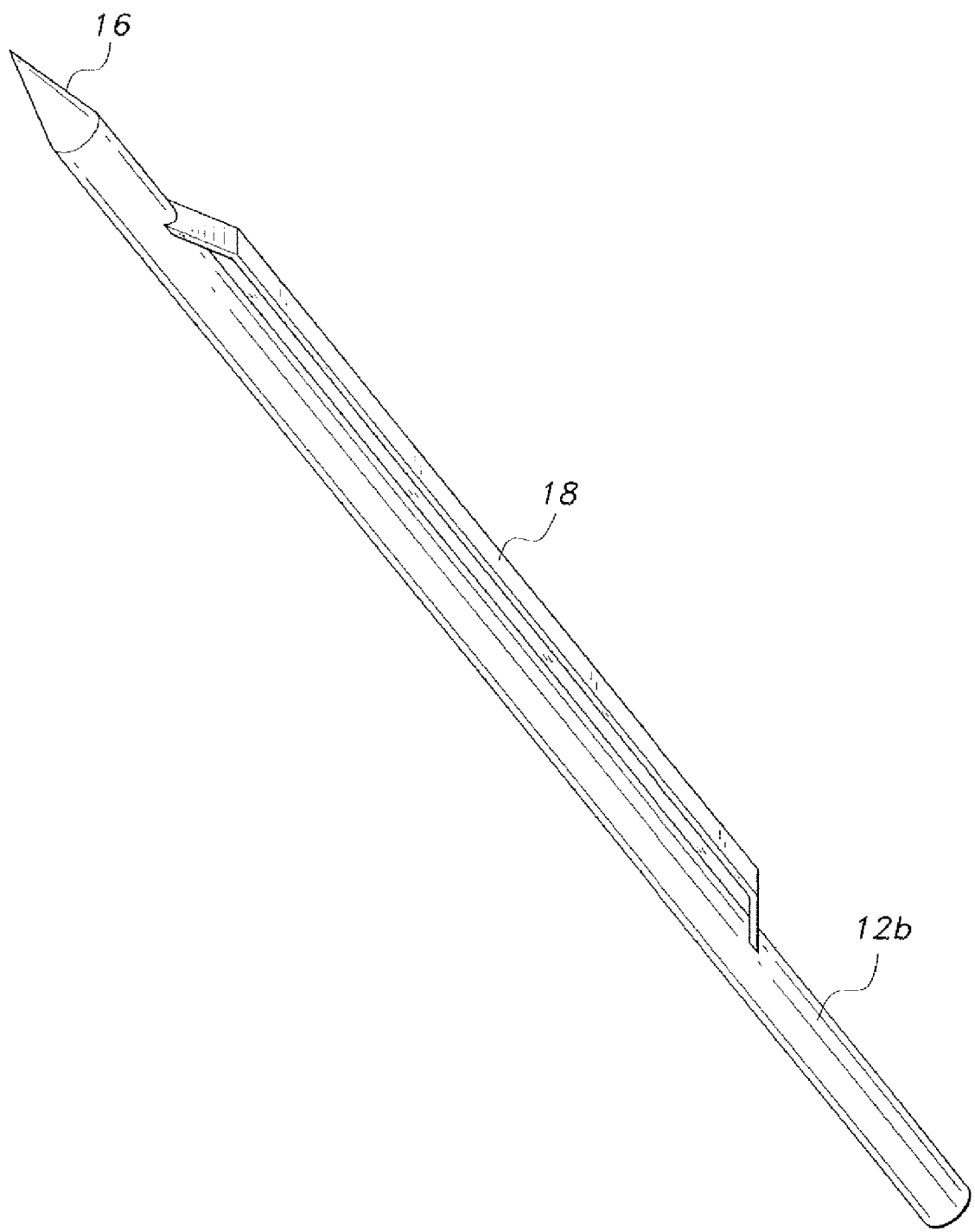
FIG. 3 is a perspective view of an alternative embodiment of the shaft-fin arrangement according to the present invention.

The meat tenderness tester 10 (shown in FIG. 1) is a hand held tool that includes a rotatable elongate shaft 12a which can be stuck into meat at a precise depth and rotated by a torque sensing motor M disposed in the tool 10. The shaft 12a has various configurations that allow it to be inserted into the meat and withdrawn without destroying the meat being tested. Fin-like members 14a (shown in FIGS. 1 and 2) disposed on the shaft 12a create a measurable resistance to rotation that is measured by sensors associated with motor M disposed inside housing body 104 of the tool 10. On-off trigger switch 102 is arranged on the housing 104 in a manner that facilitates activation of the unit 10 with a user's thumb as his fingers are curled around undulating finger grip portion 111 of the housing 104.

Figure 4:
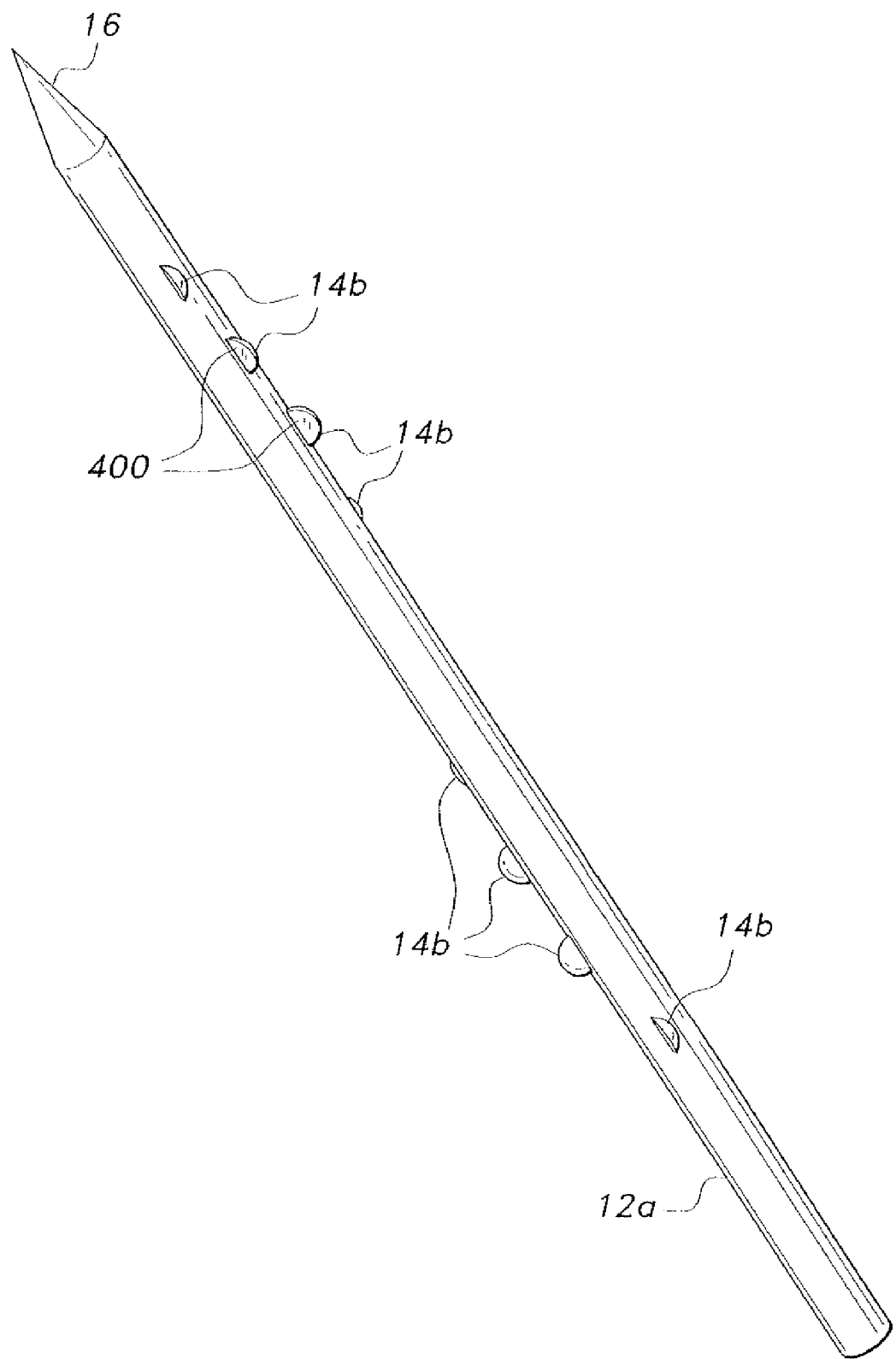
FIG. 4 is a perspective view of an alternative embodiment of helically arranged fins on the shaft according to the present invention.

The motor M is electrically connected to the trigger switch 102 and a power source is activated when the trigger switch 102 is switched to an ON position. The motor M is mechanically coupled to the removable shaft 12a and begins to rotate the shaft 12a a measured rotational displacement when the shaft 12a is inserted into a carcass or portion thereof. Torque resistance is provided by half cylindrical cross-sectioned fins 14a of shaft 12a, or by quarter spherical periphery fins 14b (shown in FIG. 4), which provide an alternative configuration of shaft 12a. An alternative shaft design 12b may include an elongate fin 18. In the fin embodiments shown in FIGS. 1, 2, and 4, the fins are arranged in a helical configuration along the surface of the shaft 12a. Surface 400 of quarter spherical periphery fins 14b may be flat as shown in FIG. 4, or may be concave so that the configuration of each fin 14b is like that of a scoop which could potentially add more torque resistance as the fins 14b impinge portions of carcass while the shaft 12a is rotated.

A control system included in motor-sensor device M may either move the motor M a specific rotational amount and measure the amount of voltage/current required to do so, or alternatively, may provide a specific voltage/current combination and measure the resultant angular displacement produced. Either arrangement calibrates torque resistance to the toughness, tenderness of the meat in which the shaft is inserted during rotation.

A digital display 100 on the housing body 104 reads out this mechanical resistance (torque) in a calibrated measurement of the shear forces encountered by the rotating shaft 12a (or 12b); the measurement indicating a degree of tenderness of the meat cut being tested. Both shafts 12a and 12b have a tapered, pointed end 16 allowing either shaft 12a or shaft 12b to be inserted and withdrawn from the test meat without damaging the meat product under test.

A convex shaped shield 110 is disposed on the housing 104 near where the probe inserts into the housing 104, the shield 110 acting as a barrier which shields an operator from meat product detritus which may be flung in the direction of the operator while the rotating shaft 12a (or 12b) is engaging the test subject.

It is to be understood that the present invention is not limited to the embodiments described above, but encompasses any and all embodiments within the scope of the following claims.

I claim:

1. A meat tenderness tester, comprising:
   a housing body having grip and thumb rest external portions adapted for holding by a user's hand;
   a motor disposed inside the housing body;
   a sensor in operable communication with said motor, the sensor transmitting information about torque resistance encountered by said motor;
   a digital display in operable communication with said sensor, said digital display indicating said torque resistance information;

an elongate shaft removably coupled to said motor, said elongate shaft extending away from said housing body when coupled to said motor, portion of said coupled elongate shaft distal from said motor having a tapered pointed end to facilitate insertion of said shaft into a portion of meat carcass;

at least one fin disposed along said shaft, said at least one fin adding torque resistance to rotation of said shaft when said shaft is rotated in a solid medium; and an electrical trigger switch disposed on said thumb rest portion of said housing body, said electrical trigger switch being in operable communication with said motor to activate and deactivate said motor when depressed/released by said user's thumb, causing said shaft to rotate a measured amount when said motor is activated.

2. The meat tenderness tester according to claim 1, further comprising a convex shaped shield disposed on the housing near a probe insertion end of the housing said convex shaped shield acting as a barrier which shields an operator from meat product detritus which may be flung in the direction of the operator while the rotating shaft is engaging the meat carcass.

3. The meat tenderness tester according to claim 1, wherein said at least one fin comprises an elongate blade member having tapered ends.

4. The meat tenderness tester according to claim 1, wherein said at least one fin comprises a plurality of fins arranged in a helical configuration along the surface of the shaft.

5. The meat tenderness tester according to claim 4, wherein each of said plurality of fins has a peripheral surface area formed from a cylindrical section of said each of said plurality of fins.

6. The meat tenderness tester according to claim 4, wherein each of said plurality of fins has a peripheral surface area formed from a spherical section of said each of said plurality of fins.

7. The meat tenderness tester according to claim 6, wherein said each of said plurality of fins includes a concave exposed surface forming a scoop that impinges portions of said meat carcass as said shaft is rotated.

* * * * *